United States Patent [19]

Alburger

[11] 3,988,924

[45] Nov. 2, 1976

[54] METHOD OF REGENERATING AN INSPECTION PENETRANT SOLVENT

[76] Inventor: James R. Alburger, 5007 Hillard Ave., La Canada, Calif. 91011

[22] Filed: Aug. 20, 1975

[21] Appl. No.: 606,285

Related U.S. Application Data

[63] Continuation-in-part of Ser. No. 577,323, May 14, 1975, which is a continuation-in-part of Ser. No. 327,559, Jan. 29, 1973, abandoned.

[52] U.S. Cl. .................................. 73/104; 134/10; 134/12
[51] Int. Cl.² ..................... G01N 21/16; B08B 7/04
[58] Field of Search ................ 73/104; 134/10, 12; 252/301.2 P, 408; 356/237

[56] References Cited
UNITED STATES PATENTS

| | | | |
|---|---|---|---|
| 3,422,670 | 1/1969 | Alburger | 73/104 |
| 3,554,020 | 1/1971 | Fijalkowski | 73/104 |
| 3,751,970 | 8/1973 | Alburger | 73/104 X |
| 3,764,265 | 10/1973 | Fijalkowski | 73/104 X |
| 3,888,693 | 6/1975 | Schevey et al. | 134/10 |
| 3,926,044 | 12/1975 | Alburger | 73/104 |
| 3,935,731 | 2/1976 | Alburger | 73/104 |
| 3,949,601 | 4/1976 | Alburger | 73/104 |

*Primary Examiner*—S. Leon Bashore
*Assistant Examiner*—Marc L. Caroff

[57] ABSTRACT

Water solutions of certain glycol-ether-type materials having negative temperature coefficients of water solubility are used as solvent removers in an inspection penetrant process. The concentration of the glycol-ether-type material in the water is controlled and adjusted by thermostatically controlling the temperature of a solvent remover reservoir containing water and an excess of the glycol-ether-type material. Excess glycol-ether-type material separates by flotation, carrying with it any dissolved penetrant, leaving a bottom layer of purified and re-usable solvent remover solution. The top layer of glycol-ether-type material may be further purified by distillation and reflux condensation to remove contaminants of dye, penetrant, and other foreign materials.

9 Claims, No Drawings

METHOD OF REGENERATING AN INSPECTION PENETRANT SOLVENT

This application is a continuation-in-part of my copending application Ser. No. 577,323, filed May 14, 1975, for "Inspection Penetrant Process Using Solvency-Inhibited Remover Compositions", which was a continuation-in-part of application Ser. No. 327,559, filed Jan. 29, 1973, for "Solvency-Inhibited Remover Compositions and Process for Inspection Penetrants", now abandoned.

RELATED PATENTS AND PATENT APPLICATIONS

U.S. Pat. No. 3,107,298, for APPARATUS FOR THE MEASUREMENT OF FLUORESCENT TRACER SENSITIVITY.

U.S. Pat. No. 3,311,479, for PENETRANT INSPECTION PROCESS AND COMPOSITIONS.

U.S. Pat. No. 3,341,705, for METHOD OF CONTROLLING THE THICKNESS OF APPLIED THIN LIQUID FILMS USING DYE TRACERS.

U.S. Pat. No. 3,386,920, for PROCESS FOR FLUORESCENCE DETECTION OF EXTREMELY THIN TRACER FILMS.

U.S. Pat. No. 3,527,709, for FLUORESCENT TRACER PROCESS AND COMPOSITIONS.

U.S. Pat. No. 3,530,295, for TRACER PROCESSES EMPLOYING ULTRAVIOLET ABSORBER MATERIALS.

U.S. Pat. No. 3,557,015, for DUAL-SENSITIVITY DYED LIQUID TRACERS.

U.S. Pat. No. 3,697,598, for INSPECTION PENETRANT PROCESS AND COMPOSITIONS EMPLOYING MIXTURES OF FLUORESCENT INDICATOR DYE AND NON-FLUORESCENT ULTRAVIOLET ABSORBER DYE.

Appln. Ser. No. 532,830, filed Dec. 16, 1974, for METHOD AND MEANS OF ACCELERATING REMOVAL OF BACKGROUND ENTRAPMENTS IN THE INSPECTION PENETRANT PROCESS, now U.S. Pat. No. 3,931,733.

Appln. Ser. No. 577,323, filed May 14, 1975, for INSPECTION PENETRANT PROCESS USING SOLVENCY-INHIBITED REMOVER COMPOSITIONS.

The present invention relates to a method and means of adjusting and controlling the solvent activity of a glycolether-type solvent remover composition, and purifying and recovering the used solvent remover for re-use.

In my copending appln. Ser. No. 577,323, of which the present application is a continuation-in-part, I have disclosed and claimed solvency-inhibited remover compositions which may be employed to dissolve and remove excess surface penetrant and unwanted microporosity entrapments of penetrant from test surfaces. Normally, in the solvent-remover-type penetrant process, a water-insoluble dyed liquid penetrant is applied to a test surface being inspected for the presence of crack defects. The dyed penetrant enters any cracks or flaws which are open to the surface, forming penetrant entrapments. Excess surface penetrant is removed from the test surface by draining, wiping, or pre-rinsing with a spray of water, and finally by applying a solvent remover such as alcohol, mineral thinner, or halocarbon liquid, which acts to dissolve surface residues of penetrant and flush them away. Entrapments of dyed liquid penetrant which migrate out of the surface flaws, or which are developed by absorption onto a coating of powder-type developer, may be detected visually by examination under black light in the case of fluorescent indicator dyes, or under white light in the case of visible-color indicator dyes.

A difficulty is inherent in the conventional solvent-remover inspection penetrant process, in that the solvent action of the solvent remover is so rapid that significant crack entrapments of penetrant are often stripped out within a few seconds or even within a fraction of a second following application of the solvent remover. In other words, the conventional solvent remover materials are difficult to control, since they act much too rapidly in removing surface penetrant from test parts.

The inhibited-solvency removers which are disclosed and claimed in my copending appln. Ser. No. 577,323 provide a retarded solvent action so that ample time is allowable for applying the inhibited-solvency remover to test surfaces, and for cleaning and drying the test surfaces, without an excessive stripping out of desired crack entrapments. A means for accomplishing this partial and controlled inhibition of solvent remover action is to utilize a water-soluble solvent remover or solvent-coupler material and to dilute the material with water so as to provide a specified concentration of active solvent in the water. The active solvents, or solvent couplers, utilized in the afore-said appln. Ser. No. 577,323, may be drawn from a group including various alcohols, glycols, and glycol-ethers, and the concentrations utilized may range from about 5% up to 75%.

When solvency-inhibited water solutions of the type disclosed and claimed in my appln. Ser. No. 577,323 are used to dissolve and remove penetrant from test parts, they soon become contaminated with dissolved penetrant and dyes, and gradually lose their solvent strength. In the past, it has been necessary to discard such used materials, but it would be beneficial from the standpoint of economy in chemical consumption as well as avoidance of pollution of sewage systems to regenerate and re-use the exhausted solvency-inhibited remover materials.

The principal object of the invention, therefore, is to provide a method and means for recovering and re-using solvency-inhibited remover materials.

Another object of the invention is to provide a method and means for accurately controlling the solvent activity of a solvency-inhibited remover material.

These and other objects of the invention will in part be obvious and will in part become apparent from the following description thereof.

In the present invention, I utilize as solvency-inhibited remover compositions water solutions of certain glycol-ether-type materials. For the purpose of this specification, I use the term "glycol-ether-type material" as including glycol-ethers and esters of glycol-ethers. Materials of this kind are sometimes referred to as solvent couplers, since they may exhibit features of mutual solubility for or in water, oils, and oil-soluble dyes.

I have discovered that certain of the glycol-ether-type materials exhibit very pronounced negative temperature coefficients of solubility in water. It is possible that many or even all of the known glycol-ether-type materials may exhibit negative temperature coefficients of water solubility at appropriate temperature and pressure conditions, but I have discovered that at least four of such materials exhibit the property of negative temperature coefficients of water solubility within the useful temperature range of from about 85° F. up to 210° F. These materials are; ethylene glycol monobutyl ether, diethylene glycol diethyl ether, ethylene glycol monoethyl ether acetate, and diethylene glycol monoethyl ether acetate.

A negative temperature coefficient of water solubility relates to the tendency of a material to become less soluble in water as the temperature of the mixture is raised. In the case of the glycol-ether-type materials of the present invention, their solubility as a function of temperature may be easily demonstrated and measured simply by preparing a test sample of the glycol-ether-type material having a known concentration in water, and raising the temperature of the solution until a cloudy separation begins to form. The thus-measured cloud point temperature is the maximum temperature at which the test sample concentration can be maintained. If more glycol-ether-type material is added to the mixture, the temperature being maintained at the specified cloud point, then excess glycol-ether-type material will separate from the mixture and will float to the surface to form a distinct layer, leaving the water as a bottom layer containing the glycol-ether-type material at the same cloud-point concentration. If the temperature of the mixture is raised further, then the concentration of glycol-ether-type material in the bottom layer will become progressively reduced, excess glycol-ether-type material again separating out of solution and floating to the surface to join the top-layer material. For purposes of illustration, Table I indicates the cloud point temperatures for various concentrations of several glycol-ether-type materials which are useful for the purpose of the invention.

about 3 parts water and 1 part ethylene glycol monobutyl ether. At room temperature (about 80° F.), this mixture forms a complete solution, but when the temperature of the reservoir is raised to 132° F., the mixture of liquids separates into two layers, the bottom layer having a concentration of 14.3% of the ethylene glycol monobutyl ether.

I have discovered that the top layer of more-or-less pure glycol-ether-type material which forms at elevated temperatures acts as a selective solvent for any penetrant liquid or dyes which may be dissolved in the solvent remover. Thus, in the case of a used solvent remover solution which is returned to the so-called clarifier reservoir, any dissolved penetrant and dye materials are carried into the top layer of glycol-ether-type material, leaving a bottom layer of regenerated and purified solvent remover solution. This bottom-layer liquid may be drawn off and re-used as a regenerated inhibited-solvency remover solution.

Normally, the solvent remover composition of the invention is used on test parts at room temperature or at a slightly elevated temperature which may be as high as about 120° F. or more. In special use applications, it may be found desirable to operate the inhibited-solvency remover solution at using temperatures as low as 35° F. or as high as 180° F. In any event, the operating temperature for remover usage is always somewhat lower than the temperature of the clarifier reservoir. This is for the purpose of preventing separation of the remover solution while in contact with test parts. Accordingly, the temperature of the regenerated remover solution which is drawn from the bottom layer in the clarifier reservoir is lowered to a suitable and desired remover-use temperature, and the temperature of the used remover solution is raised as the solution is re-

TABLE I

| | | CLOUD POINTS — ° F. | | | |
|---|---|---|---|---|---|
| Dilution Ratio | Concentration (%) | Ethylene Glycol Monobutyl Ether | Diethylene Glycol Diethyl Ether | Ethylene Glycol Monoethyl Ether Acetate | Diethylene Glycol Monoethyl Ether Acetate |
| 1-1 | 50 | 117 | 91 | — | 106 |
| 2-1 | 33.3 | 118 | 115 | — | 126.5 |
| 3-1 | 25 | 119.5 | 131 | — | 153 |
| 4-1 | 20 | 121.5 | 144 | — | 184 |
| 5-1 | 16.7 | 126 | 156 | 85 | — |
| 6-1 | 14.3 | 132 | 167 | 109 | — |
| 7-1 | 12.5 | 139.5 | 178 | 132 | — |
| 8-1 | 11.1 | 153 | 189.5 | 156 | — |
| 9-1 | 10.0 | >210 | 200 | 174 | — |
| 10-1 | 9.1 | — | 210 | 191 | — |
| Vapor Pressure (mm. Hg. at 25° F.) | | .88 | <1 | 1.7 | .05 |
| Evaporation Rate (Ref. BuAc = 100) | | 6 | 4 | 21 | <1 |
| Distillation Range (° C.) | | 169–173 | 184–190 | 150–160 | 214–221 |

As a result of the discovery of the feature of negative temperature coefficients of solubility which occurs in certain glycol-ether-type materials, I have found it possible to adjust and control the concentration of appropriate glycol-ether-type materials in water merely by maintaining an excess of glycolether-type material in a reservoir of water and thermostatically controlling the temperature of the reservoir to a suitable control temperature. For example, it may be desired to provide a solution of ethylene glycol monobutyl ether in water having a concentration of 14.3%. A mixture may be placed in a clarifier tank, the mixture consisting of turned to the clarifier reservoir. These changes in temperature may be effected conveniently by means of a simple tube-within-a-tube heat exchanger or by other means in accordance with known heat-exchange practice.

By withdrawing the solvent remover solution from the bottom layer in the clarifier reservoir, reducing its temperature through a heat-exchanger, collecting the remover solution in a processing tank or use-reservoir, and then returning used remover solution through the heat-exchanger to the clarifier reservoir, a circulating system may be established in which the remover solution is continuously clarified and regenerated. As long as the top layer of more-or-less pure glycol-ether-type material remains in the clarifier reservoir, any dissolved penetrant and dyes will be extracted, leaving a re-usable inhibited-solvency remover solution.

After prolonged usage and circulation of the solvency-inhibited remover solution of the invention, the top layer of glycol-ether-type material in the clarifier reservoir may accumulate a relatively high concentration of penetrant and dye materials. This solution may be bled off and discarded, being replaced with fresh glycol-ether-type material, or alternatively a suitable still device may be utilized to purify and recover the glycol-ether-type material.

Accordingly, the method and means of the invention may include several supplementary steps of distillation-recovery of the top layer of glycol-ether-type material. In practice, the accumulation of contaminants in the top layer of glycol-ether-type material takes place very slowly, so that the rate of distillation vapor transfer of this top layer material may also take place very slowly. A practical purifier still for a typical clarifier reservoir may consist of a small tubular still chamber having a volume less than a gallon of liquid. A few hundred watts of heat energy, or less, may be introduced into this still chamber to produce vaporization of the glycol-ether-type material, leaving nonvolatile penetrant oils and dyes in the still chamber. It will be understood that distillation may be made to proceed more rapidly by increasing the power input to the still. I place no limitations on the rate of distillation, since this may depend on the rate at which contaminating substances accumulate in the top liquid layer in the clarifier reservoir.

The inhibited-solvency remover solutions of the invention are characterized by relatively low solvent strengths, as compared with conventional solvent remover materials, and they will not dissolve large quantities of penetrant oils and dyes from test surfaces. Accordingly, test surfaces must be properly prepared before treatment with the inhibited-solvency remover, so as to mechanically remove the bulk of the surface penetrant, leaving only extremely thin residual films of penetrant and entrapments of penetrant in surface cracks and micro-porosities. This kind or pre-treatment may be effected by spraying the penetrant-coated test surface with plain water so as to flush off the bulk of the surface penetrant. The thus-removed penetrant and wash water are returned to the penetrant reservoir where the penetrant floats to the surface and is collected for re-use. This technique of pre-rinse removal and recovery of water-insoluble penetrants is frequently employed in penetrant processes, and is well known in the art.

I have found it possible to measure the effective average film thickness of a given fluorescent penetrant residue which remains on a test surface after a pre-rinsing treatment. A convenient method for making such measurements is to calibrate the penetrant with respect to its dimensional threshold of fluorescence transition, and then measure the apparent brightness of penetrant residues or porosity entrapments on the test surface. Calibration procedures and measurement methods of these kinds are set forth in my U.S. Pat. Nos. 3,107,298 and 3,341,705.

I have found that in the case of test parts such as JO-coated jet engine turbine blades, which exhibit severe porosity conditions, the equivalent residual film thickness of penetrant in porosity entrapments after pre-rinse treatment is typically about 0.2 microns. Many other parts, such as nickel-chrome castings, may exhibit residual films of penetrant after pre-rinsing of about .01 micron. Highly polished surfaces, which are rarely encountered in industrial inspection, may show negligable surface residues of penetrant after pre-rinsing, or they may show substantial surface residues, depending on the nature of the penetrant which is employed. In any event, following a properly applied step of pre-rinsing, the amount of penetrant which remains on a given test surface is quite small, even though it may show an extremely pronounced background of fluorescent indications, which background is often sufficient to completely obscure any actual crack indications which may be present.

It is these unwanted background indications and smears of penetrant residues which must be removed by solvent action of a remover, and I have found that water solutions of the glycol-ether-type materials of the invention will provide adequate solvent action, or rate of solution removal, at dilution ratios within the range of from about 1 to 1 up to about 20 to 1.

It will be understood that the method and means of the present invention first of all involves the use of a glycol-ether-type material dissolved in water to a specified control concentration. Second, it will be understood that at least three process steps must be carried out in repetitive rotation, these steps being:

a. Raise the temperature of a reservoir of the solvent remover solution to a control temperature sufficient to produce a separation of the remover mixture into a top liquid layer of glycol-ether-type concentrate and a bottom liquid layer of water having a controlled concentration of glycol-ether-type material.

b. Withdraw liquid from the bottom liquid layer, and lower its temperature to a desired operating temperature for treatment of test parts.

c. After using the cooled solvent remover solution to dissolve dyed liquid penetrant from test parts, raise the temperature of the used remover solution to the specified control temperature, and return the heated used remover to the solvent remover reservoir.

The aforesaid process steps serve to provide a continuous regeneration and clarification of solvent remover solution, so that it may be used and re-used in a solvency-inhibited-remover inspection penetrant process. It will be understood that supplemental steps of distillation may be carried out in repetitive rotation so as to extract and remove penetrant oils, dyes, and other dissolved materials from the top layer of glycol-ether-type liquid in the clarifier reservoir, these steps being:

d. Withdraw liquid from the top liquid layer into a still chamber.

e. Introduce heat energy into the still chamber to vaporize the glycol-ether-type material.

f. Condense the glycol-ether-type vapors, and return the thus-condensed liquid to the solvent remover reservoir.

g. Drain off and discard accumulations of nonvolatile penetrant oil, dye residues, and sludge from the still chamber.

The clarifier reservoir along with a still chamber, if such is employed, may be enclosed and sealed, leaving as the only vapor outlet a reflux condenser coil. This coil may be air cooled or water cooled so as to maintain it at a suitable low temperature such as room temperature. In this way, no vapors of any kind can escape from the apparatus beyond what might be produced by the normal room-temperature vapor pressure of the glycol-ether-type material. These vapor pressures may be quite low, as indicated in Table 1, and in a practical clarifier and still setup, it may be found that the amount of glycol-ether-type material which escapes in vapor form will be negligable. Considerably more material will be lost by carry-over or drag-out on test parts and in entrapments in the test parts as they are processed. Thus, the regenerating and recovery apparatus of the invention may provide an effectively closed circuit, except for small losses from drag-out and evaporation.

In view of the fact that some carry-over and evaporation loss of solvent remover solution occurs during the processing of test parts, it will be found necessary to replenish the solution reservoirs from time to time. A small clarifier reservoir having a volume of about 50 gallons may be entirely adequate to provide clarification and regeneration of remover solution stored in a processing tank containing several thousand gallons of solvency-inhibited remover solution. The same 50 gallon clarifier unit may be used in conjunction with a small remover dip-tank having a volume of ten gallons or less of remover solution. A single small clarifier unit may be employed to purify and regenerate a large volume of remover solution in a central reservoir tank, and this solution may be piped out to a number of processing and inspection stations in a given production facility.

When used as a solvent remover in an inspection penetrant process, the solvent remover solution of the invention may be applied to test parts by dipping, spraying, or otherwise flooding the test surfaces being processed. In any event, the used remover solution is drained from the test surfaces, and is ultimately returned to the clarifier unit where it is regenerated for re-use.

I have found that for many kinds of test parts such as jet engine turbine blades, or other aircraft parts, a concentration of about 14.3% of ethylene glycol monobutyl ether in water is about optimum for the purpose of providing a desired remover contact time in the range of about 2 to 4 minutes at room temperature. Under such conditions, the clarifier reservoir control temperature is 132° F. This temperature is easily maintained, and if a distillation step is employed the ethylene glycol monobutyl ether may be readily vaporized by means of a low-power heater element. The clarified remover solution may be easily cooled to room temperature, and test parts may be manipulated and processed in the cooled solution without undue haste. At the concentration of about 14.3%, this preferred remover solution will provide an adequate removal of unwanted background indications from porous surfaces without an excessive stripping out of desired crack indications.

Another benefit which is derived from the use of the preferred material, ethylene glycol monobutyl ether, is that it is reasonably volatile and will evaporate from test surfaces even at room temperature. Thus, after test parts are treated in the inhibited-solvency remover solution for the required contact time duration, they may be drained and dried by blowing off excess liquid using a compressed air gun, or the parts may be dried under a warm-air blower or in an oven. In any event, the parts dry rapidly, leaving well-defined flaw entrapments.

The method and means of the present invention may be employed in conjunction with any of the conventional water-insoluble post-emulsifier-type inspection penetrants, however the preferred penetrant materials are of the types which are disclosed and claimed in my U.S. Pat. No. 3,311,479. Penetrants of these kinds employ liquid vehicles which are relatively nonvolatile, although there exists a wide variety of suitable liquids which have differing boiling ranges.

For example, a preferred penetront vehicle is dimethyl naphthalene, available commercially under the trade names Hysol 4-3 or Amsco E-95. The commercial product is a mixture of isomers, and usually consists of about 66% dimethyl naphthalene, about 27% monomethyl naphthalene, about 4% polyaromatics, and a small amount of paraffinic hydrocarbons. Its boiling range is about 465° F. to 547° F., so that if it is used with ethylene glycol monobutyl ether as a solvent remover, and if a distillation step is employed, the dimethyl naphthalene will tend to remain in the still chamber, while the ethylene glycol monobutyl ether will tend to flash off to be condensed and returned to the clarifier reservoir.

Another preferred type of penetrant vehicle liquid, which is disclosed and claimed in my U.S. Pat. No. 3,311,479, is dioctyl phthalate. This, and similar liquids which are disclosed in the patent, are quite nonvolatile and extremely stable throughout the process steps of solvent extraction from the remover solution and distillation-separation from the glycol-ether-type solvent. They are therefore particularly advantageous in connection with the recovery and re-cycling process of the invention.

It will be understood that some post-emulsifier-type penetrants have low boiling points, and they are therefore not readily adaptable to distillation-separation from the solvent remover materials of the invention. When such penetrant materials are employed, they may be allowed to accumulate in the top layer of the clarifier reservoir, ultimately being bled off and discarded. Most of my preferred penetrant compositions, as taught in my U.S. Pat. No. 3,311,479, are characterized by high boiling points and low vapor pressures, so that they are easily separated by distillation from the glycol-ether-type materials of the invention.

The penetrant materials which are employed in conjunction with the solvency-inhibited removers of the invention may utilize any of the known types of indicator dyes. Visible-color indicator dyes may be used, but the preferred indicator dyes are fluorescent in character. Furthermore, these fluorescent dyes are preferably employed at high concentrations, in accordance with the teachings of my U.S. Pat. No. 3,386,920, now Re. 26,888, at concentrations sufficient to provide dimensional thresholds of fluorescence smaller than about 250 millimicrons.

I have noticed that certain of the fluorescent dyes which are commonly used as indicators in inspection penetrants, notably the coumarin-type dyes, exhibit a certain degree of solubility in water. This effect of solubility causes the dye to be leached out of penetrant entrapments in crack defects during the step of remover application, even though the penetrant liquid itself remains in the crack. Certain other types of fluorescent substances, such as those which are disclosed and claimed in my U.S. Pat. No. 3,527,709, are characterized by much lower water-solubility, and are thus capable of providing an improved resistance to leaching.

In some inspection applications, it may be desired to employ a combination of visible-color and fluorescent indicator dyes in order to provide an effect of dual-sensitivity in the penetrant. Thus, for such purposes, dye combinations of the types disclosed and claimed in my U.S. Pat. No. 3,557,015 may be employed in penetrants utilized in the process of the invention. Likewise, combinations of fluorescent and ultraviolet absorber dyes, as taught and claimed in my U.S. Pat. No. 3,697,598, or even ultraviolet absorber dyes alone, as taught and claimed in my U.S. Pat. No. 3,530,295, may be used in the penetrants employed in the process of the invention.

It will be understood that considerable variations may be encountered in optimum processing times and temperatures, depending on the preference of the user, the processing equipment which is available, the kinds of parts being processed, and other factors which may enter into consideration. For these various and combined reasons, it may be desired to operate the remover solutions of the invention at concentrations of the glycol-ether-type material as low as 5% or as high as 50% or even more. I therefore place no limits on processing conditions or concentrations of the solvent remover solutions which may be applicable.

It will be further understood that the method and means of the present invention may be combined with various other process steps which have not been specifically mentioned herein. For example, the processing sequence of pre-rinsing, solvent remover application, and final drying may be interrupted to introduce one or more steps of interim-drying in accordance with the teachings of my copending appln. Ser. No. 532,830, filed Dec. 16, 1974, for METHOD AND MEANS OF ACCELERATING REMOVAL OF BACKGROUND ENTRAPMENTS IN THE INSPECTION PENETRANT PROCESS.

Also, it will be understood that various additive substances may be included in the solvent remover solutions of the invention. For example, it may be desired to increase the viscosity of the solvent remover solution, in which case a thickener substance may be added. Suitable thickener materials may be any one of the sodium carboxymethylcellulose polymers, known commercially as "CMC". Another type of thickener gum is poly (methyl vinyl ether/maleic anhydride), known commercially as "Gantrez AN". Both of these materials are soluble in cold or hot water, and will remain in water solution in the presence of substantial amounts of the glycol-ether-type materials of the invention. They are both available in a range of molecular weights, the preferred molecular weights being the higher values which provide high solution viscosities at low concentrations.

Many of the conventional water-soluble gums, such as methyl cellulose or ethyl hydroxyethyl cellulose tend to precipitate from solution at elevated temperatures or in the presence of added glycol-ether-type materials, and these are therefore unsuitable as thickeners. For the water-soluble gums which are suitable for use in the remover solutions of the invention, it is usually possible to achieve a satisfactory increase in viscosity at gum concentrations in the range of about 0.2% up to about 3%.

Finally, it will be understood that the preferred glycol-ether-type solvent material is ethylene glycol monobutyl ether, and its preferred clarifier control temperature is within the range of about 120° F. to 155° F., yielding concentrations of solvent within the range of about 23% to 11%.

Although the invention has been described with respect to specific embodiments thereof, it will be understood that various changes and modifications may be made without departing from the spirit of the invention and the scope of the appended claims.

I claim:

1. In an inspection penetrant process which includes the steps of (1) applying a water-insoluble dyed liquid penetrant to test surfaces, (2) applying a solvent remover to said penetrant-treated test surfaces to dissolve and remove excess surface penetrant, leaving entrapments of penetrant in any surface cracks which may be present, and (3) inspecting said test surfaces for the presence of flaw-entrapment indications, the improvement which comprises the following steps carried out in repetitive sequence:
    a. Raise the temperature of a reservoir of said solvent remover to a control temperature sufficient to produce a separation of said remover into a top liquid layer of glycol-ether-type concentrate and a bottom liquid layer of water having a controlled concentration of glycol-ether-type material,
    b. Withdraw liquid from said bottom liquid layer, and lower the temperature of said withdrawn liquid to a desired operating temperature for treatment of test surfaces,
    c. After using said cooled solvent remover to dissolve dyed liquid penetrant from said test surfaces, raise the temperature of the used remover solution to the said control temperature, and return said used remover to said solvent remover reservoir, said solvent remover comprising a mixture in water of a glycol-ether-type solvent liquid having a negative temperature coefficient of water solubility.

2. A method in accordance with claim 1, in which supplemental steps of distillation are carried out in repetitive rotation as follows:
    d. withdraw liquid from said top layer into a still chamber.
    e. introduce heat energy into said still chamber to vaporize said glycol-ether-type concentrate material.
    f. condense said glycol-ether-type concentrate vapors, and return the thus-condensed liquid to the said remover reservoir.
    g. drain off and discard accumulations of nonvolatile penetrant oil, dye residues, and sludge from said still chamber.

3. A method in accordance with claim 1, in which said glycol-ether-type liquid is at least one member selected from the group consisting of ethylene glycol monobutyl ether, diethylene glycol diethyl ether, ethylene glycol monoethyl ether acetate, and diethylene glycol monoethyl ether acetate.

4. A method in accordance with claim 1, in which said glycol-ether-type liquid is ethylene glycol monobutyl ether.

5. A method in accordance with claim 1, in which said control temperature is maintained within the range of from about 85° F. up to about 210° F.

6. A method in accordance with claim 1, in which the concentration of said glycol-ether-type liquid in water is adjusted to a value within the range of from about 50% down to about 5%.

7. A method in accordance with claim 1, in which said desired operating temperature for treatment of test surfaces falls within the range of about 35° F. up to about 180° F.

8. A method in accordance with claim 1, in which said glycol-ether-type liquid is ethylene glycol monobutyl ether and said control temperature is maintained within the range of from about 120° F. to 155° F., to provide an active solvent concentration in the solvent remover solution within the range of about 23% to about 11%.

9. A method in accordance with claim 1, in which said solvent remover mixture contains an added water-soluble thickener gum to a concentration within the range of about 0.2% up to about 3%.

* * * * *